US010045500B2

(12) United States Patent
DeWachter

(10) Patent No.: US 10,045,500 B2
(45) Date of Patent: Aug. 14, 2018

(54) GLYPHOSATE TOLERANT SOYBEAN VARIETY

(71) Applicant: Richard DeWachter, Otterville (CA)

(72) Inventor: Richard DeWachter, Otterville (CA)

(73) Assignee: 2331535 ONTARIO LTD, Otterville, Ontario (CA)

( * ) Notice: Subject to any disclaimer, the term of this patent is extended or adjusted under 35 U.S.C. 154(b) by 367 days.

(21) Appl. No.: 14/837,343

(22) Filed: Aug. 27, 2015

(65) Prior Publication Data
US 2016/0057961 A1    Mar. 3, 2016

Related U.S. Application Data

(60) Provisional application No. 62/043,192, filed on Aug. 28, 2014.

(51) Int. Cl.
*A01H 5/10*    (2018.01)

(52) U.S. Cl.
CPC ...................... *A01H 5/10* (2013.01)

(58) Field of Classification Search
None
See application file for complete search history.

(56) References Cited

U.S. PATENT DOCUMENTS

| | | | | |
|---|---|---|---|---|
| 6,590,143 B2* | 7/2003 | Eby | ........................... | A01H 5/10 435/415 |
| 7,135,626 B2* | 11/2006 | Davis | ........................ | A01H 1/04 800/300 |
| 7,465,857 B1* | 12/2008 | van 't Klooster | ........ | A01H 5/10 800/260 |

* cited by examiner

*Primary Examiner* — David H Kruse

(74) *Attorney, Agent, or Firm* — Schwabe Williamson & Wyatt, PC

(57) ABSTRACT

A glyphosate-tolerant annual soybean (*Glycine max*) variety, in one example known as soybean variety '210342', seed used to produce the soybean, and methods of using the soybean plant and the seed are provided. Weed control in areas planted with the disclosed soybeans can be achieved by direct application of glyphosate herbicides.

27 Claims, 2 Drawing Sheets

GLYPHOSATE TOLERANT SOYBEAN VARIETY

CROSS REFERENCE TO RELATED APPLICATION

This application claims the benefit of U.S. Provisional Patent Application No. 62/043,192, filed Aug. 28, 2014, which is incorporated herein by reference in its entirety.

FIELD

This disclosure relates to a new and distinctive soybean variety, '210342', that is tolerant to glyphosate at levels sufficient to remove grass and broadleaf weed species from soybean fields.

BACKGROUND

The soybean (*Glycine max*) is a species of legume native to East Asia and widely grown for its edible bean. Varieties of soybeans are used for many purposes, including being processed into soybean meal and vegetable oil. Traditional fermented food uses of soybeans include soy sauce, fermented bean paste, natto, and tempeh, among others. Examples of non-fermented food uses include soy milk, tofu and tofu skin. Soybeans are thus a globally important crop, providing oil and protein. To maximize crop yield weeds must be controlled.

Glyphosate (N-(phosphonomethyl) glycine) is the active ingredient in glyphosate herbicides, such as ROUNDUP® brand herbicide produced by Monsanto (St. Louis, Mo.) or TOUCHDOWN® brand herbicides produced by Syngenta (Greensboro, N.C.). Typically, glyphosate is formulated as a water-soluble salt such as an ammonium, alkylamine, alkali metal or trimethylsulfonium salt. One of the most common formulations is the isopropylamine salt of glyphosate, which is the form employed in ROUNDUP® brand herbicide. TOUCHDOWN® brand herbicides utilize a formulation of either the trimethylsulfonium, potassium or diammonium salt of glyphosate.

Glyphosate is a broad spectrum herbicide that inhibits the enzyme 5-enolpyruvyl shikimate-3-phosphate synthase (EPSPS). It is conventionally applied as an aqueous solution to the foliage of plants, where it is taken up into the leaves and transported throughout the plant. Commercial formulations of glyphosate may also include one or more surfactants to facilitate penetration of the active ingredient into the plant leaves, as well as compounds to enhance rainfastness. Numerous U.S. patents disclose various formulations of glyphosate, including U.S. Pat. Nos. 4,405,531; 5,118,338; 5,196,044; 5,639,711; 5,652,197; 5,679,621; and 5,750,468.

Little success has been reported in finding natural resistance to glyphosate herbicides in plants. This is beneficial in one respect since it indicates that the likelihood of glyphosate resistant populations of weeds arising is low, but it also means that few naturally resistant desirable plant species are available. Thus, great care must be taken when applying glyphosate herbicides in the vicinity of desirable plants (such as crops, ornamentals, and grass) to avoid crop damage.

SUMMARY

Herein disclosed is an annual soybean (*Glycine max* (L.) Merr.) variety, which is sufficiently glyphosate tolerant to survive applications of glyphosate herbicides at levels sufficient to kill many common grass and broadleaf weeds that grow in soybean fields. One example of such a glyphosate tolerant annual soybean is soybean variety '210342'. As used herein, a glypho sate-tolerant annual soybean is capable of tolerating application of herbicide at effective rates. Particular examples of "herbicide effective application rates" include, but are not limited to, at least about 0.72 liters per acre, at least about 1 liter per acre, at least about 1.25 liters per acre, but not greater than 1.44 liters per acre of agricultural grade formulations of glyphosate-based herbicides (such as TOUCHDOWN® TOTAL, Syngenta, Greensboro, N.C., containing 500 g/L of glyphosate: N-(phosphonomethyl) glycine, equivalent to application of approximately 4.17 lb/gal acid equivalent of glyphosate). The disclosed annual soybean is also low population tolerant.

In one example, the annual soybean variety '210342' is tolerant to application of at least about 0.72 liters per acre, such as at least about 0.8 liters per acre, 0.9 liters per acre, 1 liter per acre, 1.1 liters per acre 1.2 liters per acre, 1.25 liters per acre, 1.3 liters per acre, 1.4 liters per acre, 1.44 liters per acre or 1.5 liters per acre of agricultural grade formulations of glyphosate-based herbicides (equivalent to application of about 0.79 lb/gal, 0.88 lb/gal, 0.99 lb/gal, 1.11 lb/gal, 1.21 lb/gal, 1.32 lb/gal, 1.37 lb/gal, 1.43 lb/gal, 1.54 lb/gal, 1.58 lb/gal or 1.65 lb/gal acid equivalent of glyphosate, respectively). In another example, soybean variety '210342' is tolerant to application of between about 1 liter per acre and about 1.5 liters per acre, such as between about 1.1 liters per acre and about 1.44 liters per acre, including between about 1.25 liters per acre and 1.44 liters per acre, between about 1.25 liters per acre and about 1.3 liters per acre, of agricultural grade formulations of glyphosate-based herbicides. In another example, soybean variety '210342' is tolerant to application of at least about 1 liter per acre of agricultural grade formulations of glyphosate-based herbicides, such as at least about 1.25 liters per acre (equivalent to application of approximately 1.1 lb/gal and 1.37 lb/gal acid equivalent of glyphosate, respectively). In another example, soybean variety '210342' is tolerant to application of no more than 1.44 liters per acre of agricultural grade formulations of glyphosate-based herbicides (equivalent to application of approximately 1.58 lb/gal acid equivalent of glyphosate).

A deposit of the new soybean variety '210342' was made with the American Type Culture Collection (ATCC), 10801 University Blvd., Manassas, VA, 20110. The date of deposit is Mar. 7, 2018. The deposit was of 100 packets of seeds, with 25 seeds in each packet. The deposit is intended to meet all of the requirements of 37 C.F.R.§§ 1.801-1.809. The accession number for those deposited seeds of the new soybean variety '210197' is ATCC Patent Deposit Designation PTA-124877. The deposit will be maintained in the depository for a period of 30 years, or 5 years after the last request, or for the effective life of the patent, whichever is longer, and will be replaced if necessary during that period. In one embodiment, the disclosure provides soybean seed deposited as ATCC Patent Deposit Designation PTA-124877, as well as bulk soybean seed containing such seeds. The variety is also maintained at 2331535 Ontario LTD, 732664 Pick Line, Otterville, Ontario NOJ-1R0.

In one example, the disclosure provides annual soybean plants that include, and in some examples consist of, or consist essentially of, the morphological and physiological characteristics of the annual soybean known as variety '210342', as well as seeds of such plants. In another example, the disclosure provides annual soybean plants having the genotype of '210342'. The disclosure also encompasses annual soybean plants produced by crossing '210342' with other soybean varieties, as well as seeds of such plants. The present disclosure also provides methods of producing soybean seed that include planting seed from '210342' under conditions that result in the germination of the seed, growth of soybean plants and setting of progeny seed, and then harvesting the progeny seed.

The disclosure also provides annual soybean plants produced by exposing '210342' to at least 0.72 liters per acre of agricultural grade formulations of glyphosate-based herbicides, or greater amounts, such as at least about 0.72 liters per acre, such as at least about 0.8 liters per acre, 0.9 liters per acre, 1 liter per acre, 1.1 liters per acre, 1.2 liters per acre, 1.3 liters per acre, 1.4 liters per acre, or 1.44 liters per acre of agricultural grade formulations of glyphosate-based herbicides, and selecting those plants which survive such exposures. These methods can be used to identify soybean plants that can tolerate applications of agricultural grade formulations of glyphosate-based herbicides, such as at least 0.7, such as at least about 0.72 liters per acre, such as at least about 0.8 liters per acre, 0.9 liters per acre, 1 liter per acre, 1.1 liters per acre, 1.2 liters per acre, 1.3 liters per acre, 1.4 liters per acre, or 1.44 liters per acre of agricultural grade formulations of glyphosate-based herbicides.

The disclosure also provides a tissue culture of regenerable cells of the new soybean variety '210342', as well as plants regenerated therefrom. Such regenerated soybean plants can include or consist of the physiological and morphological characteristics of a plant grown from the seed of the new soybean variety '210342'. Exemplary regenerable cells include but are not limited to those from protoplasts or cells, such as those from embryos, meristematic cells, pollen, leaves, roots, root tips, anther, pistil, flower, seed, cotyledon, hypocotyl, shoot, or stem of the new soybean variety '210342'.

A method is provided for producing a glyphosate-tolerant soybean plant by crossing a first soybean plant with one or more other soybean plants to produce progeny soybean plants, wherein the first soybean plant is a '210342' variety or a glyphosate-tolerant cross derived from an '210342' variety, and then screening the progeny soybean plants to select a progeny soybean plant that is tolerant to glyphosate. Glyphosate-tolerant soybean plants produced by this method are also encompassed by the disclosure.

Methods of producing soybean seed from the '210342' soybean plants are provided. In some examples such methods include crossing '210342' with itself or a second soybean plant and harvesting a resulting soybean seed. In some examples, the second soybean plant has one or more desirable traits, which is/are introduced into plants and seeds resulting from such a cross. For example, the second plant can be transgenic, wherein the transgene confers the desirable trait(s). Seeds produced by such methods, including $F_1$ hybrid seeds, as well as soybean plants or parts thereof produced by growing such a seed, are provided. In some examples, the method of crossing includes planting seeds of the new soybean variety '210342', cultivating soybean plants resulting from the seeds until the plants bear flowers, allowing fertilization of the flowers of the plants; and harvesting seeds produced from the plants.

Methods are provided for developing a new soybean plant using the new '210342' variety. For example, the methods can include using '210342' plants or parts thereof as a source of breeding material in plant breeding techniques, such as recurrent selection, mass selection, bulk selection, backcrossing, pedigree breeding, genetic marker-assisted selection and genetic transformation. In some examples, a plant of the new soybean variety '210342' is used as the male or female parent.

The disclosure provides a first generation ($F_1$) hybrid soybean seed produced by crossing a plant of the new soybean variety '210342' to a second soybean plant. In some embodiments, the $F_1$ hybrid soybean plant is grown from the hybrid seed produced by crossing the new soybean variety '210342' to a second soybean plant. In specific examples, provided is a seed of an $F_1$ hybrid plant produced with the new soybean variety '210342' as one parent, the second generation ($F_2$) hybrid soybean plant grown from the seed of the Fi hybrid plant, and the seeds of the $F_2$ hybrid plant.

Methods of producing hybrid soybean seeds are also provided. In one example, the method includes crossing the new soybean variety '210342' to a second, distinct soybean plant which is nonisogenic to the new soybean variety '210342'. In some examples, the method includes cultivating soybean plants grown from seeds of the new soybean variety '210342' and cultivating soybean plants grown from seeds of a second, distinct soybean plant, until the plants bear flowers. A flower on one of the two plants is cross pollinated with the pollen of the other plant, and the seeds resulting from such a cross are harvested.

The disclosure also provides soybean plants and parts thereof produced by any of the methods disclosed herein. Thus, provided herein are plants of soybean variety '210342' that further include a single locus conversion, such as one or more desired traits, for example produced by backcros sing or genetic transformation. In some embodiments, the soybean plants produced by the disclosed methods includes at least two, at least three, at least four, at least five, or at least 10 of the traits of the new soybean variety '210342' as described herein. In some embodiments, the soybean plants produced by the disclosed methods include at least two, at least three, at least four, at least five, or at least 10 of the traits of the new soybean variety '210342' such as glyphosate tolerance, as described herein.

Methods of producing a commodity plant product are provided. In some examples the method includes obtaining or supplying a plant of the new soybean variety '210342', or a part thereof, and producing the commodity plant product therefrom. In some examples the method includes growing and harvesting the plant, or a part thereof. Exemplary commodity plant products include but are not limited to a protein concentrate, a protein isolate, soybean hulls, meal, flour or oil.

The foregoing and other features and advantages of the disclosure will become more apparent from the following description, which proceeds with reference to the accompanying figures.

DETAILED DESCRIPTION

Description of Terms

Figure 1:
FIG. 1 is a digital image of DH410 (row A), S20-G7 (row B), '210342' (row C) and Thames (row D) plants prior to application of 1¼ /L/acre of 500 g/L glyphosate.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants and reference to "the seed" includes reference to one or more seeds and equivalents thereof known to those skilled in the art, and so forth. . The term "or" refers to a single element of stated alternative elements or a combination of two or more elements, unless the context clearly indicates otherwise. For example, the phrase "A or B" refers to A, B, or a combination of both A and B.

Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Backcross: The mating of a hybrid to one of its parents. For example hybrid progeny, for example a first generation hybrid ($F_1$), can be crossed back one or more times to one of its parents. Backcrossing can be used to introduce one or more single locus conversions (such as one or more desirable traits) from one genetic background into another.

Cell. Cell as used herein includes a plant cell, whether isolated, in tissue culture or incorporated in a plant or plant part.

Cross. Synonymous with hybridize or crossbreed. Includes the mating of genetically different individual plants, such as the mating of two parent plants.

Cross-pollination: Fertilization by the union of two gametes from different plants.

$F_1$ hybrid: The first generation progeny of the cross of two nonisogenic plants.

Gene Silencing. A general term describing epigenetic processes of gene regulation, including any technique or mechanism in which the expression of a gene is prevented.

Genotype. The genetic constitution of a cell, an organism, or an individual (i.e., the specific allele makeup of the individual) usually with reference to a specific character under consideration.

Lodging: The visual rating of the uprightness of the plants. The score is based on the average of the plants in a plot with a score of 1 to 5, with a score of 1 indicating all plants are erect, and a score of 5 where over about 80% of the plants in a plot are prostrate.

Maturity date: The evaluation of plants considered as mature when about 95% of the pods have reached their mature color.

Plant: Includes reference to an immature or mature whole plant, including a plant from which seed, roots or leaves have been removed. Seed or embryo that will produce the plant is also considered to be the plant.

Plant height. Plant height is taken from the top of the soil to the tip of the plant, and is typically measured in centimeters or inches.

Plant parts. Includes protoplasts, leaves, stems, roots, root tips, anthers, pistils, seed, embryo, pollen, ovules, cotyledon, hypocotyl, flower, shoot, tissue, petiole, cells, calli, pods, meristematic cells and the like. Includes plant cells of a tissue culture from which soybean plants can be regenerated.

Progeny. Offspring; descendants.

Regeneration. The development of a plant from tissue culture. The cells may, or may not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Relative maturity: Refers to the maturity grouping designated by the soybean industry over a given growing area. This figure is generally divided into tenths of a relative maturity group. Within narrow comparisons, the difference of a tenth of a relative maturity group equates very roughly to a day difference in maturity at harvest.

Seed. The part of a flowering plant that typically contains the embryo with its protective coat and stored food and that can develop into a new plant under the proper conditions; fertilized and mature ovule.

Seed quality: The visual rating of the completeness of the seed. The score is based on the completeness of the seed coat and overall soundness of the seed. Scores range from 1 to 5, with a score of 1 indicating good quality seed and a score of 5 indicating the seeds are of poor quality.

Seed yield: The yield in bushels/acre (bu/a) and is the actual yield of the grain at harvest.

Self-pollination: The transfer of pollen from the anther to the stigma of the same plant.

Single locus converted (conversion) plant: Plants developed by backcrossing and/or by genetic transformation, wherein essentially all of the desired morphological and physiological characteristics of a soybean variety are recovered in addition to the characteristics of the single locus transferred into the variety via the backcrossing technique.

Tissue culture: A composition that includes isolated cells of the same or a different type or a collection of such cells organized into parts of a plant.

Transformation. The introduction of new genetic material (e.g., exogenous transgenes) into plant cells. Exemplary mechanisms that are to transfer DNA into plant cells include (but not limited to) electroporation, microprojectile bombardment, *Agrobacterium*-mediated transformation and direct DNA uptake by protoplasts.

Transgene. A gene or genetic material that has been transferred into the genome of a plant, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a soybean plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

EXAMPLES

The following examples are provided to better describe the present disclosure and to guide those of ordinary skill in the art in the practice of the present disclosure.

Example 1

Origin and Breeding History

Soybean variety '210342' began as a cross between the sister lines 0301 and 0306 in 2001. Sister lines 0301 and 0306 were derived from a cross of Crusher and Legacy in 1999. Bulk and modified single plant descent methods were used in developing the variety. F1 seed from promising progeny were collected end planted in 2002. F2 seed from the best 5 plants was collected, pooled and planted in 2003. Single plant selection was done from 2003 through to the final selection in 2007. Seed from this selection was used to increase seed supply. Every year the best 3 to 5 plants were selected for breeding. All field testing was done in Otterville, Ontario. Plots of 3 rows with a row length of 60 meters and row spacing of 40 cm were used in the field trials. Section criteria included plant phenotype, agronomic performance and seed yield.

Soybean variety '210342' was been found to be uniform and stable in plant morphology. Exceptions were an occasional plant with grey pubescence, less than 1 per 1000. It has been uniform and stable for the last 5 generations.

Example 2

Distinction Statement for '210342'

The variety '210342' is similar to the check varieties DH410SCN, Thames, and S20-G7 in that it has approximately the same height and plant shape when planted at conventional populations. All four evaluated varieties were also non-genetically modified organisms (GMO). Where '210342' was distinct, was when it was planted at extremely low populations it had the ability to compensate and not suffer a significant yield loss. It was also distinct in that it has a natural tolerance to glyphosate herbicide. When sprayed at recommended label rates, the check varieties were killed, whereas '210342' the majority of plants survived and were able to grow back.

Example 3

Seed Deposit

Seeds of the soybean variety referred to herein as '210342', were deposited with the ATCC (Manassas, VA; Patent Deposit Designation PTA-124877). The variety is also maintained at 2331535 Ontario LTD, 732664 Pick Line, Otterville, Ontario NOJ-1R0.

Example 4

Morphological Characteristics

The morphological characteristics of soybean variety '210342' are shown in Tables 1 below. Soybean plants were established, arranged and maintained as detailed in Example 1. At 137 days maturity, plant height for soybean variety '210342' was 40 cm. Variations on these measurements may be observed for plants of differing ages, grown in other locations, or under different prevailing weather conditions.

TABLE 1

Plant Morphological Measurements in Soybean variety '210342'

| Morphology | |
|---|---|
| Seed Shape | Spherical-Flattened (L/W ratios >1.2; L/T ratios ≤1.2) |
| Seed Coat Color | Yellow |
| Seed Coat Luster | Dull |
| Seed Size | 17.4 grams/100 seeds |
| Hilum Color | Black |
| Cotyledon Color | Green |
| Hypocotyl Color | Green |
| Leaf Color | Dark Green |
| Flower Color | White |
| Pod Color | Brown |
| Pubescence Color | Brown (Tawny) |
| Plant Type | Bushy |
| Plant Height | Medium |
| Plant Growth Type | Indeterminate |
| Plant Habit | Erect to semi-erect |
| Maturity Group | II |
| Maturity Subgroup | 3 |

Example 5

Glyphosate Tolerance

This example provides methods and results of field trials in which the glyphosate tolerance characteristics of soybean variety '210342' were examined and compared with the most similar variety Thames as well as other similar varieties DH410SCN and/or S20-G7.

Figure 2:
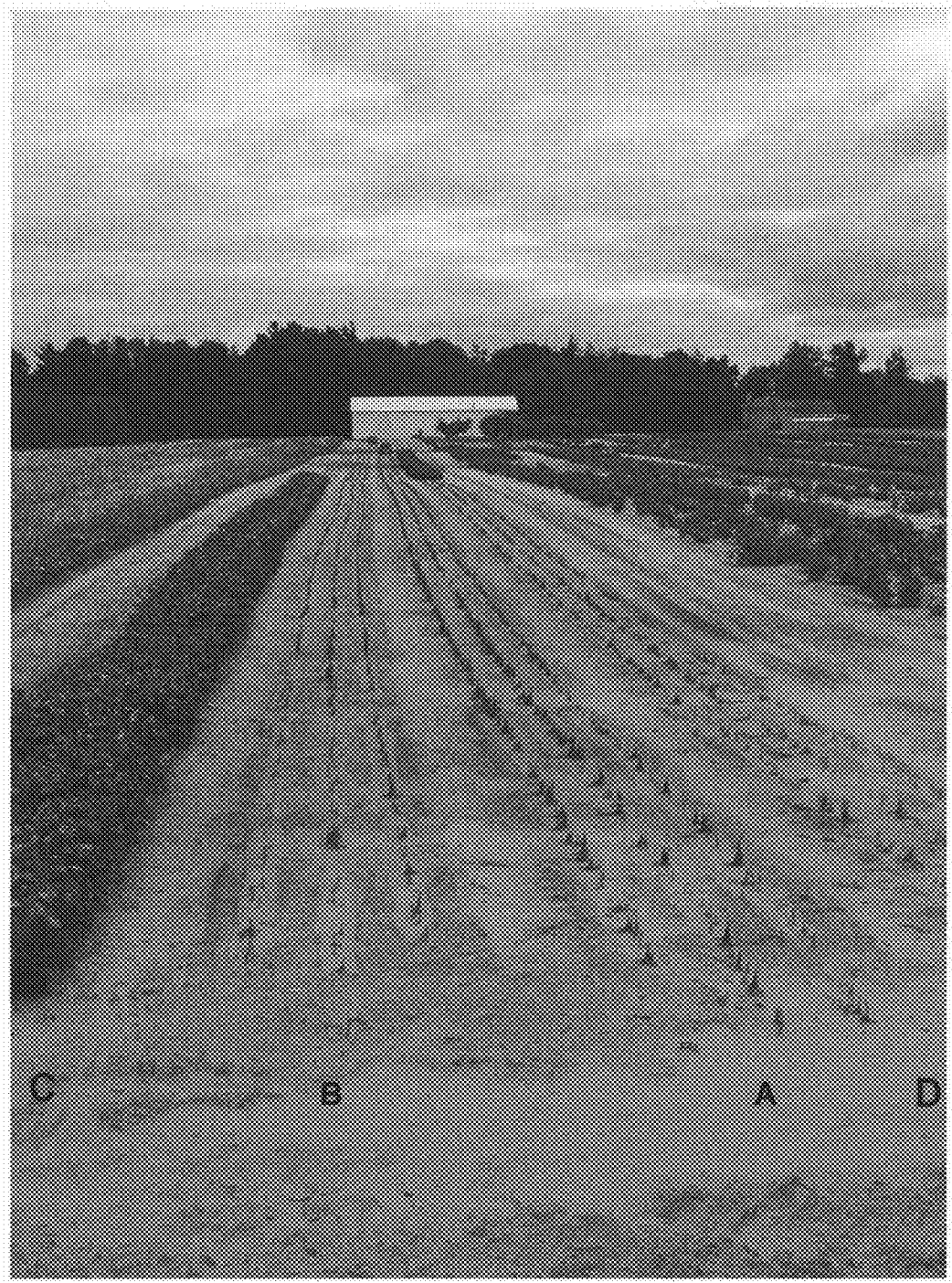
FIG. 2 is a digital image illustrating typical plant survival in a glyphosate tolerance trial following application of 1¼ /L/acre of 500 g/L glyphosate. As illustrated, '210342' was the only survivor in row C as compared to S20-G7 (row B), DH410 (row A) and Thames (row D) after nine days of treatment.

In 4 trials, '210342' was compared to Thames, DH410 and S20-G7. All plots were 3 rows wide (15/ rows)×200 feet long. Plots were sprayed with TOUCHDOWN TOTAL™ at a rate of 1.25 of product per acre. TOUCHDOWN TOTAL™ is a glyphosate herbicide with a concentration of 500 g/L of glyphosate. All checked varieties (Thames, DH410 and S20-G7) were completely controlled. The majority of 201342 plants showed damage to the growing point, but recovered. Final yields were 0 for all checked varieties (Thames, DH410 and S20-G7) and varied from 19 to 48 bu/acre for '210342' depending on the plot (See FIGS. 1 and 2). The plot that yielded 19 bu/acre received extensive damage from deer feeding at an early stage of growth. These studies illustrate that '210342' is glyphosate tolerant.

Example 6

Low Population Tolerance

This example provides methods and results of field trials in which the low population characteristics of soybean variety '210342' were examined and compared with the most similar variety Thames. These studies demonstrate that soybean variety '210342' is low population tolerant.

Field #2 Description

This field was planted in May and was harvested in November. It was planted in 30' rows and had thinned to approximately 16,000 plants per acre based on seed drop. Plot 4 and 5 are loamy sand with poor water holding capacity Plot size was 0.12 acres. Final population was 17,400 for Plot 3 (Thames), with a final yield of 21.69 bu/acre and 15,660 for Plot 4 (Thames), with a final yield of 24.747 bu/acre. Final population for Plot 1 ('210342') was 14,810, with a final yield of 33.36 bu/acre and 16,552 for Plot 2 ('210342') and 33.3 bu/acre. Plot 8 was coarse sand with very poor water holding capacity. Plot size was also 0.12 acres in size. Final population was 14,810 for Plot 8 (Thames) had a final population of 17,400 and a yield of 14.41 bu/acre.

When calculating yield versus population in Plot 3 and 4, Plot 3 (Thames) had an average of 34 grams of seed per plant and Plot 4 (Thames) had an average of 43 grams of seed per plant versus. In comparison, Plot 1 ('210342') had an average of 61.43 grams of seed per plant and Plot 2 ('210342') had an average of 54.87 grams of seed per plant.

In conclusion, '210342' was dramatically more able to maintain yield in low population as compared to similar variety Thames. These studies illustrate that '210342' is capable of thriving in low population.

Example 7

Production of Glyphosate-Tolerant Soybean Plants

Soybean variety '210342' plants can be grown under normal conditions for growing similar soybean varieties, and bulk seed for large-scale planting can be obtained by methods known in certified seed production. For example, bulk seed can be produced by planting '210342' variety seeds obtained from ATCC (Accession Number PTA124877) or 2331535 Ontario LTD, 732664 Pick Line, Otterville, Ontario NOJ-1R0, allowing the mature plants to produce seed by self-pollination and then collecting the seed. Standard precautions should be taken to prevent cross-pollination from other soybeans, such as growing the variety in an isolated plot of sterilized soil, removing adjacent vegetation, etc.

To confirm maintenance of the glyphosate-tolerance characteristic, a glyphosate herbicide (containing 500 g/L active ingredient glyphosate or 4.17 lb/gal acid equivalent of glyphosate) can be applied to the plants at the equivalent of at least about 1.25 liters per acre.

Example 8

Production of Low Population Tolerant Soybean Plants

Soybean variety '210342' plants can be grown under normal conditions for growing similar soybean varieties, and bulk seed for large-scale planting can be obtained by methods known in certified seed production. For example, bulk seed can be produced by planting '210342' variety seeds obtained from ATCC (Accession Number PTA 124877) or 2331535Ontario LTD, 732664 Pick Line, Otterville, Ontario NOJ-1R0, allowing the mature plants to produce seed by cross-pollination with each other and then collecting the seed. Standard precautions should be taken to prevent cross-pollination from other soybeans, such as growing the variety in an isolated plot of sterilized soil, removing adjacent vegetation, etc.

To confirm maintenance of the low population-tolerance characteristic, plants would be subjected to a low population planting (e.g., 30,000 plants per acre). Plants that generated on average 50 grams of seeds per plant in the conditions would be identified as low population plants.

Example 9

Exemplary Uses of the Glyphosate Tolerant Soybean Variety '210342'

The annual soybean variety '210342' can be used in the same way as other annual soybean varieties. However, the tolerance to glyphosate herbicides affords '210342' variety particular advantages over other varieties. For example, with current commercially available varieties of non-GMO soybean varieties, the preparation of a soybean crop that is to be made by seeding requires extensive preparation of the soil to remove weeds that may be present. With soybean variety '210342', such preparation can be avoided since some weeds that begin to grow in the field are readily removed by application of a glyphosate herbicide. With soybean variety '210342', glyphosate herbicides can also be used to remove many of the most troublesome weeds such as annual grasses (such as foxtail, barnyard grass, crabgrass, fall panicum, proso millet woolly cup grass), annual broadleaves (such as velvetleaf, common ragweed, common lamb's-quarters, redroot pigweed, smooth pigweed, cocklebur, green smartweed, lady's-thumb, Pennsylvania smartweed, eastern black nightshade, wild mustard, wild buckwheat), perennials (such as quack grass, field bindweed, common milkweed, sowthistle, Canada thistle, wirestem muhly and yellow nutsedge). Thus, soybean variety '210342' is especially marketable and therefore useful.

Over 90% of soybeans grown in the United States are genetically modified to accept the use of glyphosate herbicides, however not all countries and markets accept genetically modified soybeans. The disclosed '210342' variety solves this problem by still allowing farmers to use glyphosate herbicides, but because this variety is not genetically modified, it is still acceptable to all markets.

Example 10

Introducing Traits of '210342' Into Other Soybean Varieties

The morphological and physiological characteristics of the soybean variety '210342', including the glyphosate tolerance trait, can be introduced into other soybean varieties by conventional breeding techniques. For example, the '210342' variety can be grown in pollination proximity to another variety of soybean, allowing cross-pollination to occur between the '210342' variety and the other variety, and then harvesting the hybrid seeds. Plants grown from these hybrid seeds can then be tested for the maintenance of the molecular characteristics described above for the '210342' variety, or the plants can simply be observed to see if they display the same characteristics described in the above tables.

For example, plants grown from these hybrid seeds can be tested for glyphosate tolerance by application of glyphosate herbicide at various levels. In this way, the glyphosate tolerance characteristic can be combined with other desirable plant characteristics. Thus, the provision of '210342' enables the production of progeny plants of '210342' having the glyphosate tolerance characteristic. "Progeny plants" of '210342' are any plants that are the offspring of a cross between '210342' and any other plant or plants. Progeny plants also include successive generations of the offspring, for example those selected for glyphosate tolerance using the methods described herein. First-generation progeny plants may retain the glyphosate tolerance characteristic of the '210342' parent. However, if a first-generation progeny plant does not retain the desired level of glyphosate tolerance observed with '210342', subsequent generations of offspring can be recycled for glyphosate tolerance which have at least the same resistance characteristics of '210342' described herein, such capable of tolerating application of at least about 1.25 liters per acre of a glyphosate herbicide (containing 500 g/L active ingredient glyphosate). In one example, subsequent generations of offspring can have a glyphosate tolerance that exceeds that of '210342', for example capable of tolerating application of at least about 0.72 liters per acre, for example at least about 1.25 liters per acre, for example up to about 1.44 liters per acre of a glyphosate herbicide (containing 500 g/L active ingredient glyphosate or 4.17 lb/gal acid equivalent of glyphosate).

In addition, soybean variety '210342' can be used as transformation targets for the production of transgenic soybeans. In certain examples, the present disclosure contemplates the transformation of cells derived from the '210342' variety with at least one transgene. Transgenes that can be used, include, but are not limited to, transgenes that confer resistance to herbicides, insect, disease (viral, bacterial, fungal, nematode) or drought resistance, standability, prolificacy, salt damage resistance, and quality. Examples of such genes and methods of transforming plants are described in U.S. Pat. No. 6,025,545 to Lundquist et al. and Jain and Jain (*Indian J. Exp. Biol.* 38:6-17, 2000) herein incorporated by reference.

Having illustrated and described the principles of the disclosure in multiple embodiments and examples, it should be apparent to those skilled in the art that the disclosure can be modified in arrangement and detail without departing from such principles. The invention, therefore, encompasses all modifications coming within the spirit and scope of the following claims

I claim:

1. A soybean plant of soybean variety '210342', representative sample seed of the variety is deposited under American Type Culture Collection (ATCC) Accession No. Patent Deposit Designation PTA-124877.

2. Seed of the soybean plant of claim 1.

3. A seed mixture, comprising the seed of claim 2.

4. A vegetative sprig or clone of the soybean plant of claim 1.

5. A soybean plant produced from the soybean plant of claim 1 by introducing a transgene that confers upon the soybean plant resistance to a herbicide, bacterial disease, viral disease, fungal disease, nematode, or insect.

6. A soybean plant produced from the soybean plant of claim 1 by introducing a transgene that confers upon the soybean plant drought tolerance or salt tolerance.

7. Seed resulting from crossing the soybean plant of claim 1 with a second soybean plant.

8. A soybean plant grown from the seed of claim 7.

9. A method of producing soybean seed, comprising
planting the seed of claim 2 under conditions that result in the germination of the seed, growth of soybean plants and setting of progeny seed; and
harvesting the progeny seed.

10. A method of producing a glyphosate-tolerant soybean plant, comprising:
crossing a first soybean plant with at least one other soybean plant to produce progeny soybean plants, wherein the first soybean plant is the soybean plant of claim 1;
screening the progeny soybean plants to select a progeny soybean plant that is tolerant to glyphosate.

11. A glyphosate-tolerant soybean plant produced by the method of claim 10.

12. A vegetative sprig or clone of the glyphosate-tolerant soybean plant of claim 11.

13. The glyphosate-tolerant progeny soybean plant produced by the method of claim 10, wherein the progeny soybean plant is tolerant to glyphosate and comprises at least one transgene that confers upon the soybean plant resistance to a herbicide, bacterial disease, viral disease, fungal disease, nematode or insect.

14. The glyphosate-tolerant progeny soybean plant produced by the method of claim 10, wherein the progeny soybean plant is tolerant to glyphosate and comprises at least one transgene that confers upon the soybean plant drought tolerance or salt tolerance.

15. The glyphosate-tolerant soybean plant of claim 11, wherein the soybean plant is tolerant to application of at least about 0.79 pound/gallon acid equivalent of glyphosate.

16. The glyphosate-tolerant soybean plant of claim 11, wherein the soybean plant is tolerant to application of at least about 1.25 pound/gallon acid equivalent of glyphosate.

17. The glyphosate-tolerant soybean plant of claim 11, wherein the soybean plant is tolerant to application of at least about 1.58 pound/gallon acid equivalent of glyphosate.

18. A seed of soybean variety '210342', representative sample seed of the variety is deposited under American Type Culture Collection (ATCC) Patent Deposit Designation PTA-124877.

19. A method of producing soybean seed, comprising
planting the soybean seed of claim 18 under conditions that result in the germination of the soybean seed, growth of soybean plants and setting of progeny seed; and
harvesting the progeny seed.

20. A soybean plant germinated from the seed of claim 19.

21. A soybean plant produced from the soybean plant of claim 20 by transformation with a transgene that confers upon the soybean plant resistance to a herbicide, bacterial disease, viral disease, fungal disease, nematode, or insect.

22. A soybean plant produced from the soybean plant of claim 20 by transformation with a transgene that confers upon the soybean plant drought tolerance or salt tolerance.

23. A method of producing a glyphosate-tolerant soybean plant, comprising:
exposing the soybean plant of claim 1 to at least about 0.79 pound/gallon acid equivalent of glyphosate, thereby generating exposed soybean plants;
selecting exposed soybean plants that are tolerant to the glyphosate.

24. The method of claim 23, wherein the soybean plant of claim 1 is exposed to at least about 1.25 pound/gallon acid equivalent of glyphosate.

25. The method of claim 23, wherein the soybean plant of claim 1 is exposed to at least about 1.58 pound/gallon acid equivalent of glyphosate.

26. A method of producing a commodity plant product comprising:

obtaining the soybean plant of claim 1 or a part thereof; and producing the commodity plant product therefrom.

27. The method of claim 26, wherein the commodity plant product is protein concentrate, protein isolate, soybean hulls, meal, flour or oil.

\* \* \* \* \*